United States Patent

Rieveley

[11] Patent Number: 6,153,632
[45] Date of Patent: Nov. 28, 2000

[54] METHOD AND COMPOSITION FOR THE TREATMENT OF DIABETES

[76] Inventor: Robert B. Rieveley, 4102 Yuculta Crescent, Vancouver, British Columbia, Canada, V6N 3R5

[21] Appl. No.: 08/804,903

[22] Filed: Feb. 24, 1997

[51] Int. Cl.[7] .................. A61K 31/425; A61K 38/28; A61K 31/175; A61K 31/155
[52] U.S. Cl. .................. 514/369; 514/3; 514/592; 514/635; 514/866
[58] Field of Search .................. 514/3, 369, 592, 514/866, 635

[56] References Cited

U.S. PATENT DOCUMENTS

| 4,708,868 | 11/1987 | Brickl et al. | 514/309 |
| 4,849,405 | 7/1989 | Ecanow | 514/3 |
| 4,873,080 | 10/1989 | Brickl et al. | 514/315 |
| 4,963,526 | 10/1990 | Ecanow | 514/3 |
| 5,206,219 | 4/1993 | Desai | 514/3 |
| 5,422,125 | 6/1995 | Skyler et al. | 426/646 |
| 5,595,763 | 1/1997 | Guinovart et al. | 424/617 |

OTHER PUBLICATIONS

Weinstock et al., Pioglitazone. In vitro effects on rat hepatoma cells and in vivo liver hypertrophy in KKAy mice, (1997) abstract.

Windolz et al., The Merck Index, Tenth Ed. (1983) pp. 723 and 724, abstract No. 4866.

*Primary Examiner*—Kevin E. Weddington
*Attorney, Agent, or Firm*—Oyen Wiggs Green & Mutala

[57] ABSTRACT

This invention is directed to a novel method and composition for the treatment of diabetes mellitus (Type I, Impaired Glucose Tolerance ["IGT"] and Type II). More specifically, this invention pertains to a novel method of treating diabetes mellitus by incorporating a therapeutic amount of one or more insulin sensitizers along with one or more of an orally ingested insulin, an injected insulin, a sulfonylurea, a biguanide or an alpha-glucosidase inhibitor for the treatment of diabetes mellitus.

24 Claims, No Drawings

METHOD AND COMPOSITION FOR THE TREATMENT OF DIABETES

TECHNICAL FIELD OF THE INVENTION

This invention is directed to a novel method and composition for the treatment of diabetes mellitus (Type I, Impaired Glucose Tolerance ["IGT"]and Type II). More specifically, this invention pertains to a novel method of and compositions for orally treating diabetes mellitus by administering to a person afflicted with diabetes mellitus one or more sensitizer chemicals, which increase the cells ability to utilize glucose, along with orally ingested medications for the treatment of diabetes mellitus.

BACKGROUND OF THE INVENTION

It is estimated that 1.5 to 2% of the entire population of the world suffers from diabetes mellitus of some type. Diabetes mellitus is a chemical disorder of the human body primarily involving an inability of the body to properly utilize sugar and other chemical compounds in the metabolism of the body. It is characterized by an elevation in the concentration of sugar in the blood and also by the appearance of sugar in the urine.

In general terms, diabetes mellitus is classified into three types, namely, Type I, IGT and Type II. In Type I diabetes, the beta cells in the pancreas, probably through an autoimmune reaction, cease producing insulin into the bloodstream of the person. Insulin is a chemical substance which is normally secreted into the bloodstream by beta cells within the pancreas. Insulin is vitally important to the person because it enables the person to properly utilize and consume sugar in the bloodstream as part of the metabolism process.

In Type I cases, where the pancreas has ceased producing insulin, it is necessary for the afflicted person to inject insulin directly into the bloodstream at prescribed periodic intervals and dosages in order to control the level of sugar in the blood. This is called intravenous injection. Oral ingestion of insulin is also possible but usually less effective due to the degradation of insulin caused by the passage through the stomach and upper intestine.

In IGT and Type II diabetes, the pancreas continues to produce insulin but, some or all of the insulin may fail to bind to the body's cell receptors and/or internalization of insulin in the cells is reduced. In such cases, there may be a sufficient level of insulin in the blood, but the ability of the cells to uptake glucose is reduced or non-existent because of reduced internalized insulin.

The existence of Type I, IGT or Type II diabetes in a person is usually determined by an oral glucose tolerance test (OGTT). OGTT is a test in which the fasting patient is given a known amount of glucose (sugar) by mouth, and the blood is tested at intervals thereafter to note the quantity of sugar in the blood. A curve is then constructed from which important information about the person can be drawn. The glucose tolerance test curve will typically show whether the patient is hyperglycaemic (diabetic) or whether the patient has too little sugar in his or her blood and is therefore hypoglycaemic.

Symptoms of hyperglycaemia can be headaches, increased urination, thirst, nausea, weight loss, fatigue and coma. Hyperglycaemia can be caused by Hypoinsulinism, a condition in which the insulin producing beta cells of the pancreas fail to manufacture insulin or manufacture and secrete a reduced amount of insulin into the bloodstream. In such cases, levels of sugar in the blood are dramatically increased.

Hyperglycaemia can also be caused by failure of some or all of the available insulin in the blood to bind to the body's cell receptors and/or internalization of insulin in the cells is reduced.

Hypoglycaemia (too little sugar) is also a blood condition that diabetics must constantly guard against. The symptoms of hypoglycaemia are abrupt episodes of intense hunger, trembling of the hands and body, faintness, black spots before the eyes, mental confusion, sweating, abnormal behaviour, and, in severe cases, convulsions with loss of consciousness. In such cases, examination of the blood at the time of these attacks will show an extremely low level of circulating sugar in the blood.

Hypoglycaemia can be caused by Hyperinsulinism, a condition in which the insulin producing beta cells of the pancreas manufacture and secrete an excessive amount of insulin into the bloodstream. Levels of sugar in the blood are therefore dramatically reduced.

Transfer of glucose from the blood stream to the body cells is believed to be enabled by the binding of insulin to the cell receptors. Receptor bound insulin then increases the amount of insulin that is internalized in the cell. Internalized insulin results in increased utilization of glucose in the cell and consequently increased metabolism. A drug that sensitizes the surface of a body cell to increase the cell's internalization of insulin or is believed or purported to function by sensitizing a cell to insulin is known herein as an "insulin sensitizer".

The following is a list of drugs that are being or have been tested as insulin sensitizers:

1. BRL-49653 as produced by SmithKine Beecham or by some other advocate.
2. Pioglitazone HCL as produced by Takeda or some other advocate.
3. Troglitazone, Noscal or Resiline as produced by Sankyo, Glaxo Wellcome or Warner-Lambert.
4. MC 555 as produced by Mitsubishi or some other advocate.
5. ALRT 268 as produced by Ligand or some other advocate.
6. LGD 1069 as produced by Ligand or some other advocate.
7. Chromic Picolinate.
8. Diab II™ (otherwise known as V-411) or Glucanin and produced by Biotech Holdings Ltd. or Volque Pharmaceutical.
9. Vanadyl Sulfate (Vanadium Oxysulfate).
10. Chromic Polynicotinate.

Intravenous injection is the anathema of all Type I and II diabetics forced to inject insulin. These diabetics today are cursed to a lifelong ritual of having to inject insulin into their bloodstream, usually several times a day, in order to keep the level of insulin in the blood within prescribed levels.

Considerable research is being conducted to develop an insulin which can be orally ingested for the treatment of Type I or II diabetes. Such an orally ingestible insulin would be welcomed by Type I and Type II diabetics because it would no longer be necessary for them to undergo a daily routine of intravenous insulin injections. Unfortunately, to date, an orally ingested insulin has not yet been successfully developed.

A major problem is that stomach acids and gut enzymes of the person destroy most of the orally ingested insulin and hence the amount of ingested insulin that reaches the bloodstream is less than what is therapeutically required for the diabetic to function normally. Time release systems, which protect the insulin while it passes through the stomach and upper intestine, and release the insulin subsequently, are being researched to alleviate this problem. The theory of these time release systems is to incorporate the insulin with appropriate time release mechanisms so the insulin is not released until after the time release-insulin combination has passed through the stomach and the preliminary stages of the digestive process.

IGT and Type II Diabetes can be treated with one or more classes of drugs generally known as hypoglycaemics to reduce blood glucose levels.

One class of hypoglycaemics are known as "sulfonylureas". Trade-marks for commercially available sulfonylureas include Glucotrol, Diabinese, DiaBeta, Micronase, Tolinase and Orinase. Sulfonylureas appear to stimulate the pancreas and increase the production of insulin from the beta cells in the pancreas. Unfortunately, there are potential unfavourable side effects from the use of sulfonylureas. Therefore, the less a patient is required to use a sulfonylurea, the fewer side effects are likely to be experienced by that patient.

Another class of hypoglycaemics are known as "biguanides". Trade-marks for some commercially available biguanides include Metformin and Glucophage. The physiological action of biguanides is not completely understood. However, biguanides may divert glucose before reaching the blood stream thereby reducing blood glucose levels. Biguanides may also increase cell receptor sensitivity. There are potential unfavourable side effects from the use of biguanides by a patient so the less a patient uses a biguanide, the less likely the patient is to experience unfavourable side effects.

A further class of hypoglycaemics is known as the "alpha-glucosidase inhibitors". Trade-marks for some alpha-glucosdidase inhibitors include Precose, Prandase, and Acrabose. These drugs are believed to bind glucose in the gastrointestinal tract thereby reducing glucose absorption. Because there are unfavourable side effects associated with the use of alpha-glucosidase inhibitors, the less a patient uses such drugs, the less the patient is likely to experience unfavourable side effects.

The following U.S. patents are relevant to the art of orally administered insulin:

U.S. Pat. No. 4,362,719 —Therapeutic Method and Compositions for the Treatment of Juvenile Diabetes Mellitus U.S. Pat. No. 4,579,730 —Pharmaceutical Compositions Containing Insulin U.S. Pat. No. 4,602,043 —Treatment for Hypoglycemia U.S. Pat. No. 4,696,815 —Anti-Diabetic Pharmaceutical Forms and the Preparation Thereof U.S. Pat. No. 4,708,868 —Anti-Diabetic Pharmaceutical Forms and the Preparation Thereof U.S. Pat. No. 4,826,684 —Composition for, and Method of, Treatment of Diabetes U.S. Pat. No. 4,849,405 —Oral Insulin and a Method of Making the Same U.S. Pat. No. 4,871,739 —Substituted 6H-7,8-dihydrothiapyrano (3,2-D) -pyrimidines as Hypoglycemic Agents U.S. Pat. No. 4,873,080 —Oral Anti-Diabetic Pharmaceutical Compositions and the Preparation Thereof U.S. Pat. No. 4,963,526 —Oral Insulin and a Method of Making the Same U.S. Pat. No. 4,978,667 —Substituted 6H-7,8-dihydrothiapyrano (3,2-d)-pyrimidines as Hypoglycemic Agents U.S. Pat. No. 5,057,517 —Piperazinyl Derivatives of Purines and Isosteres Thereof as Hypoglycemic Agents U.S. Pat. No. 5,187,154 —Diagnosis and Treatment of Humans with Diabetes or at Risk to Develop Diabetes U.S. Pat. No. 5,206,219 —Oral Compositions of Proteinaceous Medicaments U.S. Pat. No. 5,234,906 —Hyperglycemic Compositions U.S. Pat. No. 5,284,845 —Use of Oral Diazoxide for the Treatment of Disorders in Glucose Metabolism U.S. Pat. No. 5,380,526 —Antidiabetic Agent and Method of Treating Diabetes U.S. Pat. No. 5,422,125 —Method and Composition for Treatment of Insulin Resistance Syndromes U.S. Pat. No. 5,424,406 —Dihydrochalcone Derivatives which are Hypoglycemic Agents U.S. Pat. No. 5,444,086 —Naphthalenylmethyl Thiophenones as Antihyperglycemic Agents U.S. Pat. No. 5,468,755 —Therapeutic Process for the Treatment of the Pathologies of Type II Diabetes U.S. Pat. No. 5,478,852 —Use of Thiazolidinedione Derivatives and Related Antihyperglycemic Agents in the Treatment of Impaired Glucose Tolerance in Order to Prevent or Delay the Onset of Noninsulin-Dependent Diabetes Mellitus U.S. Pat. No. 5,510,360 —Azolidinediones as Antihyperglycemic Agents U.S. Pat. No. 5,532,256 —New Azolidinediones and Thiadiazolidinediones as Antihyperglycemic Agents U.S. Pat. No. 5,589,183 —Method and Apparatus for Treatment of Neurogenic Diabetes Mellitus, and Other Conditions U.S. Pat. No. 5,595,763 —Tungsten (VI) Compositions for the Oral Treatment of Diabetes Mellitus

SUMMARY OF INVENTION

The invention is directed to a method and composition for the treatment of diabetes mellitus including Type I, IGT and Type II diabetes mellitus. More specifically, this invention pertains to a novel method of treating diabetes mellitus by incorporating a therapeutic amount of one or more insulin sensitizers along with one or more of an orally ingested insulin, an injected insulin, a sulfonylurea, a biguanide or an alpha-glucosidase inhibitor for the treatment of diabetes mellitus. A therapeutic amount of insulin sensitizer can comprise one microgram to 10 grams of one or more insulin sensitizers combined or used with one or more of:

a. A therapeutically effective amount of an orally ingestible insulin which withstands degradation by passage through the stomach and upper intestine of the mammal so that a therapeutically effective level of insulin reaches the bloodstream of the mammal. The addition of the insulin sensitizer is to sensitize the cells of the mammal so as to enhance insulin uptake and/or utilization of glucose by the cells of the mammal thus reducing the orally ingested insulin required for a therapeutic dose, and/or, b. An injected insulin product. The addition of the insulin sensitizer is to sensitize the cells of the mammal so as to enhance insulin uptake and/or utilization of glucose by the cells of the mammal thus reducing the therapeutic dose required of injected insulin, and/or, c. A sulfonylurea. The addition of the insulin sensitizer is to sensitize the cells of the mammal so as to enhance insulin uptake and/or utilization of glucose by the cells of the mammal thus reducing the required therapeutic dose of the sulfonylurea, and/or, d. A biguanide. The addition of the insulin sensitizer is to sensitize the cells of the mammal so as to enhance insulin uptake and/or utilization of glucose by the cells of the mammal thus reducing the required therapeutic dose of the biguanide, and/or, e. A alpha-glucosidase inhibitor. The addition of the insulin sensitizer is to sensitize the cells of the mammal so as to enhance insulin uptake and/or utilization of glucose by the cells of the mammal thus reducing the required therapeutic dose of the alpha-glucosidase inhibitor.

The invention is directed to a method for the treatment of diabetes mellitus comprising administering to a person afflicted with diabetes mellitus a therapeutic amount of an insulin sensitizer with a therapeutic amount of a drug selected from the group consisting of: (a) an orally ingestible insulin; (b) an injectible insulin; (c) a sulfonylurea; (d) a biguanide; and (e) an alpha-glucosidase inhibitor.

The invention is also directed to a composition for the treatment of diabetes mellitus comprising: (a) a therapeutic amount of an insulin sensitizer; and (b) a therapeutic amount of a drug selected from the group consisting of: an orally ingestible insulin; an injectible insulin; a sulfonylurea; a biguanide; and an alpha-glucosidase inhibitor.

The method and composition can include adding a pharmaceutically acceptable carrier to the composition.

DETAILED DESCRIPTION OF SPECIFIC EMBODIMENTS OF THE INVENTION

The addition of an insulin sensitizer to drugs used for the treatment of diabetes mellitus reduces the required dosage of these drugs due to the increased uptake of glucose facilitated by the insulin sensitizer.

I have discovered unexpectedly that it is possible to overcome the problem of insufficient bloodstream levels of insulin typically associated with orally ingested insulin by incorporating an orally ingestible insulin sensitizer with an orally ingestible insulin composition. While I do not wish to be bound adversely by any unsupported or invalid theories, the following description is offered as a possible explanation of why the combination of an orally ingestible insulin and an orally ingestible insulin sensitizer overcomes the problem caused by less than a therapeutic amount of insulin reaching the bloodstream when insulin is administered orally to a patient.

As discussed previously, in typical oral ingestible insulin situations to date, insufficient levels of insulin reach the bloodstream of the diabetic person because most of the insulin is destroyed in the stomach and gut of the diabetic person. However, as I have discovered, if an orally ingestible insulin sensitizer is added to the composition, and such sensitizers are not adversely affected by the strong digestive processes of the stomach and gut, the insulin sensitizer enables the lower levels of insulin that reach the bloodstream to be sufficient for purposes of enabling the cells of the body to function with the lower levels of insulin. In other words, the insulin sensitizer sensitizes the insulin insensitive cells of the body of the diabetic so that even low levels of insulin are able to attach to facilitate required glucose uptake by the cells. Hence there is sufficient glucose uptake by the cell to enable sufficient metabolism.

My discovery is also applicable to insulin injection. When insulin is injected intravenously, in combination with an insulin sensitizer, less insulin is required to achieve the same therapeutic effect in the body. The insulin sensitizer increases the utilization of glucose at any given insulin level, so less insulin is required for an equal therapeutic result.

My discovery has application to other diabetes treatments, methods and drugs. When a sulfonylurea is used to stimulate insulin production and control diabetes mellitus, including an insulin sensitizer with the sulfonylurea, less of the sulfonylurea is required to achieve the same therapeutic effect in the body. As the amount of insulin sensitizer increases the utilization of glucose at any given insulin level, less insulin is therefore required to be manufactured by the beta cells of the pancreas for an equal therapeutic result and as a result less of the sulfonylurea may be used. Adverse side effects are reduced by lower levels of sulfonylurea.

When a biguanide is used to control diabetes mellitus, the amount of the biguanide required can be reduced and yet the same blood glucose levels in the body can be achieved when an insulin sensitizer is included with the biguanide. The insulin sensitizer increases the utilization of glucose at any given insulin level. As a biguanid reduces the amount of glucose delivered to the blood, reducing the amount of the biguanid will increase the glucose delivered to the blood which can be utilized by the body due to the addition of the insulin sensitizer. Also, adverse side effects are reduced.

My discovery can also be applied to alpha-glucosidase inhibitors. When an alpha-glucosidase inhibitor is used to control diabetes mellitus, less of the alpha-glucosidase inhibitor is required to achieve the same blood glucose levels in the body when an insulin sensitizer is included. The insulin sensitizer increases the utilization of glucose at any given insulin level. Since an alpha-glucosidase inhibitor reduces the amount of glucose delivered to the blood, reducing the amount of the alpha-glucosidase inhibitor due to the addition of the insulin sensitizer will increase the level of glucose delivered to the blood which can be utilized by the body.

The subject compositions according to the invention can be administered parentally, topically or internally, but preferably orally, since that is the easiest form of administration. The compositions according to the invention may be formulated in any suitable orally acceptable form by employing conventional formulation techniques and conventional pharmaceutically acceptable formulation ingredients. The subject compositions according to the invention may, for example, be employed in nutritionally acceptable forms by incorporation of the compositions in a fibre supplement, a meal replacer, or a drink mix, or in pharmaceutically acceptable forms such as tablets or capsules in admixture with pharmaceutically acceptable carriers. The compositions according to the invention may also be used in combination with other pharmaceutically acceptable agents, for which the disclosed composition may be formulated in one unit with the other pharmaceutically effective agents, or in separate units administered at the same time or at separate times during a 24 hour period. The compositions according to the invention may be administered in single dosage form or in the form of subunits several times a day.

EXAMPLE

G. B.—Case History

G. B. is a Type I diabetic who must normally inject insulin intravenously twice a day in order to control her Type I condition. At the suggestion of the inventor, G. B. volunteered one day to determine whether or not the addition of a small amount of an insulin sensitizer to her insulin injection would enable a lower level of insulin to be administered intravenously. At 8:30 a.m., G. B. injected intravenously her usual insulin dosage and at the same time ingested 120 mg of an oral insulin sensitizer known as V-411 (sold under the trade-mark DIAB II by Biotech Holdings Ltd.). By 11:00 a.m., the same morning, G. B. went into a hypoglycaemic state involving rapid heart beat, trembling, dizzyness and other symptoms normally associated with hypoglycaemia, a condition which G. B. was familiar with. G. B. immediately started sucking sugar cubes to endeavour to raise the sugar level in her blood and alleviate the hypoglycemic condition. However, it still took about an hour for her to stabilize her hypoglycaemic condition. The proper treatment might have been for G. B. to immediately go the emergency ward of a hospital for a glucose injection.

It was clear from G. B.'s experience with the addition of the V-411 insulin sensitizer that the effects of the insulin sensitizer were very pronounced and a normal dosage of G. B.'s normal insulin injection resulted in a condition whereby the glucose in her blood was being utilized by the cells of her body at such a high rate of efficiency that she experienced a hypoglycaemic condition. It appeared clear that there was a startling effect, and indeed perhaps a synergistic effect, created between the combination of insulin and the V-411 insulin sensitizer. Thus, much smaller dosages of insulin could have been used. Indeed, it was hypothesized that such dosages could be of the same low level as experienced with orally administered insulin.

V-411 insulin sensitizer is known by the inventor to withstand the degradation effects of the gastric juices of the stomach and enzymatic action of the gut. Because of the strong or synergistic effect involving the combination of insulin and the insulin sensitizer, it follows that the inclusion of an insulin sensitizer in combination with an orally ingestible insulin should enable the orally ingestible insulin to work effectively in the treatment of diabetes mellitus. This is because the levels of insulin that must ultimately reach the bloodstream are greatly reduced, and such low levels are sufficient due to the effects of the insulin sensitizer.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A composition for the treatment of diabetes mellitus comprising:
   (a) a therapeutic amount of an insulin sensitizer; and
   (b) a therapeutic amount of an anti-diabetic agent.

2. A composition as claimed in claim 1, wherein the anti-diabetic agent is selected from the group consisting of: an orally ingestible insulin; an injectible insulin; a sulfonylurea; a biguanide; and an alpha-glucosidase inhibitor.

3. A composition as claimed in claim 2, wherein the anti-diabetic agent is insulin.

4. A composition as claimed in claim 3, wherein the insulin is injectible insulin.

5. A composition for the treatment of diabetes mellitus in a mammal comprising:
   (a) a therapeutically effective amount of an orally ingestible insulin which is formulated to withstand degradation by passage through the stomach and upper intestine of the mammal so that a therapeutically effective level of insulin reaches the bloodstream of the mammal; and,
   (b) a therapeutically effective amount of one or more of a orally ingestible insulin sensitizer which withstands degradation by the stomach contents and upper intestinal tract of the mammal and reaches the bloodstream of the mammal and thereby sensitizes the cells of the mammal to enhance insulin uptake and/or utilization of glucose by the cells of the mammal thus reducing the orally ingested insulin required for a therapeutic dose.

6. A composition for the treatment of diabetes mellitus comprising:
   (a) a therapeutically effective amount of an injected insulin; and,
   (b) a therapeutically effective amount of one or more insulin sensitizers to sensitize the cells of the mammal so as to enhance insulin uptake and/or utilization of glucose by the cells of the mammal thus reducing the therapeutic dose required of injected insulin.

7. A composition as claimed in claim 5 including a pharmaceutically acceptable carrier.

8. A composition as claimed in claim 6 including a pharmaceutically acceptable carrier.

9. A composition as claimed in claim 5 wherein the insulin is synthetic insulin.

10. A composition as claimed in claim 6 wherein the insulin is synthetic insulin.

11. A composition as claimed in claim 5 wherein the orally ingestible insulin is present in the composition in the range of about 1 mcg to 100 mg and the insulin sensitizer is present in the composition in the range of about 10 mcg to 10 mg.

12. A composition as claimed in claim 6 wherein the injected insulin is present in the composition in the range of about 1 mcg to 100 mg and the insulin sensitizer is present in the composition in the range of about 10 mcg to 10 mg.

13. Any composition as claimed in claim 5 wherein the insulin sensitizer is present in the composition in the range of about 10 mcg to 10 mg.

14. A composition as claimed in claim 6 wherein the insulin sensitizer is present in the composition in the range of about 10 mcg to 10 mg.

15. A composition as claimed in claim 1 wherein the insulin sensitizer is selected from the group consisting of BRL-49653, Pioglitazone HCL, Troglitazone, MC 555, ALRT 268, LGD 1069, Chromic Picolinate, V-411, Vanadyl Sulfate and Chromic Polynicotinate.

16. A method for the treatment of diabetes mellitus comprising administering to a person afflicted with diabetes mellitus a therapeutic amount of an insulin sensitizer with a therapeutic amount of an anti-diabetic agent.

17. A method as claimed in claim 16 comprising an insulin sensitizer and an orally ingestible insulin.

18. A method as claimed in claim 16 comprising an insulin sensitizer and an injectible insulin.

19. A method as claimed in claim 16, wherein a pharmaceutical carrier is administered to the person with the therapeutically effective amount of the anti-diabetic agent.

20. A method as claimed in claim 16, wherein the anti-diabetic agent is selected from the group consisting of:
   (a) an orally ingestible insulin;
   (b) an injectible insulin;
   (c) a sulfonylurea;
   (d) a biguanide; and
   (e) an alpha-glucosidase inhibitor.

21. A method for the treatment of diabetes mellitus comprising administering to a person afflicted with diabetes mellitus a therapeutic amount of an insulin sensitizer with a therapeutic amount of an orally ingestible anti-diabetic agent, wherein (1) the insulin sensitizer is selected from the group consisting of: BRL-49653, Pioglitazone HCL, Troglitazone, MC 555, ALRT 268, LGD 1069, Chromic Picolinate and V-411, and wherein (2) the anti-diabetic agent is selected from the group consisting of: an orally ingestible insulin; an injectible insulin; a sulfonylurea; a biguanide; and an alpha-glucosidase inhibitor.

22. The method of claim 21, wherein the insulin sensitizer is V-411.

23. The method of claim 21, wherein the anti-diabetic agent is an orally ingestible anti-diabetic agent.

24. The method of claim 22 wherein the anti-diabetic agent is an orally ingestible insulin.

* * * * *

(12) EX PARTE REEXAMINATION CERTIFICATE (6140th)
United States Patent
Rieveley

(10) Number: US 6,153,632 C1
(45) Certificate Issued: Mar. 4, 2008

(54) METHOD AND COMPOSITION FOR THE TREATMENT OF DIABETES

(76) Inventor: Robert B. Rieveley, 4102 Yuculta Crescent, Vancouver, British Columbia (CA), V6N 3R5

Reexamination Request:
No. 90/007,152, Jul. 30, 2004

Reexamination Certificate for:
Patent No.: 6,153,632
Issued: Nov. 28, 2000
Appl. No.: 08/804,903
Filed: Feb. 24, 1997

(51) Int. Cl.
*A61K 31/425* (2006.01)
*A61K 38/28* (2006.01)
*A61K 31/44* (2006.01)
*A61K 31/155* (2006.01)

(52) U.S. Cl. .................. 514/369; 514/3; 514/356; 514/635; 514/866

(58) Field of Classification Search .......... 514/3, 514/369, 592, 635, 866, 356, 188
See application file for complete search history.

(56) References Cited

U.S. PATENT DOCUMENTS

| | | | |
|---|---|---|---|
| 5,087,623 A | * 2/1992 | Boynton et al. | 514/188 |
| 5,859,037 A | * 1/1999 | Whitcomb | 514/369 |
| 5,922,769 A | * 7/1999 | Barelli et al. | 514/616 |
| 5,952,356 A | * 9/1999 | Ikeda et al. | 514/340 |
| 5,962,731 A | * 10/1999 | Boehm et al. | 562/460 |
| 5,965,584 A | * 10/1999 | Ikeda et al. | 514/342 |
| 6,150,383 A | * 11/2000 | Ikeda et al. | 514/342 |

FOREIGN PATENT DOCUMENTS

EP    0 749 751 A2 * 12/1996

OTHER PUBLICATIONS

Protest filed in U.S. Appl. No. 10/304,072, on Aug. 25, 2004, "Protest I", pp. 1–2.*
Protest filed in U.S. Appl. No. 10/304,072, on Nov. 19, 2004, "Protest II", p. 11.*
Protest filed in U.S. Appl. No. 10/304,072, on Jun. 1, 2005, "Protest III" p. 9.*
Chemical Abstracts Search Report, Registry File, American Chemical Society, completed on Jun. 25, 2005.*
U.S. Securities and Exchange Commission Form 20–F, Commission File No. 0–28974 for Biotech Holdings LTD., Processed Jan. 27, 1997, pp. 1–29.*
Biotech website archive, Jan. 1997, downloaded from http://web.archive.org/web/19980127160533/www.biotechltd.com... on Nov. 12, 2004.*

* cited by examiner

*Primary Examiner*—Raymond J. Henley, III

(57) ABSTRACT

This invention is directed to a novel method and composition for the treatment of diabetes mellitus (Type I, Impaired Glucose Tolerance ["IGT"]and Type II). More specifically, this invention pertains to a novel method of treating diabetes mellitus by incorporating a therapeutic amount of one or more insulin sensitizers along with one or more of an orally ingested insulin, an injected insulin, a sulfonylurea, a biguanide or an alpha-glucosidase inhibitor for the treatment of diabetes mellitus.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, line 66 to column 7, line 18:

G. B. is a Type I diabetic who must normally inject insulin intravenously twice a day in order to control her Type I condition. At the suggestion of the inventor, G. B. volunteered one day to determine whether or not the addition of a small amount of an insulin sensitizer to her insulin injection would enable a lower level of insulin to be administered intravenously. At 8:30 a.m., G. B. injected intravenously her usual insulin dosage and at the same time ingested 120 mg of an oral insulin sensitizer known as V-411 (sold under the trade-mark [DIAB II] *DIAB II*™ by Biotech Holdings Ltd.). By 11:00 a.m., the same morning, G. B. went into a hypoglycaemic state involving rapid heart beat, trembling, dizzyness and other symptoms normally associated with hypoglycaemia, a condition which G. B. was familiar with. G. B. immediately started sucking sugar cubes to endeavour to raise the sugar level in her blood and alleviate the hypoglycemic condition. However, it still took about an hour for her to stabilize her hypoglycaemic condition. The proper treatment might have been for G. B. to immediately go the emergency ward of a hospital for a glucose injection.

AS A RESULT OF REEXAMINATION, IT HAS BEEN DETERMINED THAT:

Claims 1–24 are cancelled.

\* \* \* \* \*